(12) United States Patent
Paulsen et al.

(10) Patent No.: US 8,663,151 B2
(45) Date of Patent: Mar. 4, 2014

(54) PERSONAL CARE DEVICES INCLUDING MOISTURE-ACTIVATED COMPOSITIONS

(75) Inventors: Jeremy David Paulsen, Neenah, WI (US); Scott W. Wenzel, Neenah, WI (US); Thomas W. Van Den Bogart, Slinger, WI (US); Jeffery Richard Seidling, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 333 days.

(21) Appl. No.: 13/033,724

(22) Filed: Feb. 24, 2011

(65) Prior Publication Data

US 2012/0220919 A1    Aug. 30, 2012

(51) Int. Cl.
*A61F 13/28* (2006.01)
*A61F 13/26* (2006.01)

(52) U.S. Cl.
CPC ............. *A61F 13/28* (2013.01); *A61F 13/26* (2013.01)
USPC ............................................................ 604/12

(58) Field of Classification Search
USPC ............................................................ 604/12
See application file for complete search history.

(56) References Cited

U.S. PATENT DOCUMENTS

| 4,300,561 | A | 11/1981 | Kaczmarzyk et al. |
| 5,533,990 | A | 7/1996 | Yeo |
| 6,515,029 | B1 | 2/2003 | Krzysik et al. |
| 6,524,269 | B2 | 2/2003 | McNamara |
| 6,592,540 | B2 | 7/2003 | DeCarlo |
| 7,226,436 | B2 | 6/2007 | Gorham et al. |
| 2002/0026140 | A1 | 2/2002 | McNamara |
| 2002/0120241 | A1 | 8/2002 | Tyrrell et al. |
| 2003/0120224 | A1 | 6/2003 | Geiser et al. |
| 2003/0135180 | A1 | 7/2003 | Nguyen et al. |
| 2003/0140430 | A1* | 7/2003 | Casperson et al. ................ 8/406 |
| 2004/0153024 | A1 | 8/2004 | Pauley et al. |
| 2005/0113780 | A1 | 5/2005 | Gatto et al. |
| 2005/0186427 | A1* | 8/2005 | Gatto .......................... 428/411.1 |
| 2005/0197617 | A1 | 9/2005 | Gorham et al. |
| 2006/0178441 | A1* | 8/2006 | Hawkins .......................... 516/77 |
| 2007/0032758 | A1 | 2/2007 | Chase et al. |
| 2007/0179429 | A1 | 8/2007 | Gorham et al. |
| 2007/0219479 | A1 | 9/2007 | Tasbas |
| 2008/0167597 | A1 | 7/2008 | Dougherty |
| 2011/0009803 | A1* | 1/2011 | Dougherty et al. ............. 604/15 |

FOREIGN PATENT DOCUMENTS

EP         1345560 B1    9/2003
WO    2005051270 A2    6/2005

OTHER PUBLICATIONS

International Search Report and Written Opinion for PCT/IB2012/050354 dated Aug. 22, 2012.
International Search Report and Written Opinion for PCT/IB2012/050355 dated Aug. 22, 2012.
Non-Final Office Action for U.S. Appl. No. 13/033,731 dated Mar. 15, 2013; 11 pages.
Final Office Action for U.S. Appl. No. 13/033,731 dated Aug. 9, 2013; 11 pages.
Code of Federal Regulations—Title 21: Food and Drugs, 21 C.F.R. 801.430 "User Labeling for Menstrual Tampons.", Apr. 13, 2011.

* cited by examiner

*Primary Examiner* — Susan Su
(74) *Attorney, Agent, or Firm* — Armstrong Teasdale LLP

(57) ABSTRACT

The present disclosure is directed to alleviating the uncomfortable and unpleasant sensations that may accompany insertion and removal of personal care devices. Specifically, the present disclosure is directed to a personal care device that includes a moisture-activated composition that becomes lubricious only upon contact with moisture, such as from mucosal surfaces in the body.

20 Claims, 6 Drawing Sheets

PERSONAL CARE DEVICES INCLUDING MOISTURE-ACTIVATED COMPOSITIONS

FIELD OF DISCLOSURE

The present disclosure is directed to alleviating the uncomfortable and unpleasant sensations that may accompany contact between personal care devices and mucosal surfaces of the body. Specifically, the present disclosure is directed to a personal care device, such as a vaginal tampon, that includes a moisture-activated composition. The composition becomes lubricious only upon contact with moisture.

BACKGROUND OF DISCLOSURE

Vaginal tampons are disposable absorbent articles sized and shaped for insertion into a women's vagina for absorption of bodily fluids generally discharged during the woman's menstrual period. There are two basic types of tampons used for feminine hygiene. The first type is a digital tampon which can be inserted without the use of an applicator. The second type is a tampon retained in an applicator wherein the tampon is inserted using the applicator.

During the insertion of vaginal tampons, the tampon, and when present, the tampon applicator, comes into contact with sensitive mucosal surfaces of the user's vaginal wall. The friction developed between the tampon and/or tampon applicator and the vaginal mucosal surfaces can cause an uncomfortable feeling of dryness. Further discomfort may be sensed during removal of the tampon as the tampon expands upon absorption of bodily fluids.

Accordingly, there is a need for a personal care device that makes usage of the device more comfortable and more desirable to the user. It would additionally be beneficial if the appearance of the personal care device during use could be improved such that the device appears less soiled.

SUMMARY OF DISCLOSURE

Many personal care devices, such as vaginal tampons, have previously been coated with compositions to improve insertion and removal of these devices. These compositions are messy and aesthetically unpleasing to the user as the compositions feel wet to the user's touch. It has now been found, however, that compositions can be prepared that only become activated upon contact with moisture from the body. More particularly, these compositions are dry to the touch, but are then made lubricious upon being contacted with the body's own moisture, allowing for a more comfortable, pleasing sensation during use of a personal care device.

Accordingly, in one embodiment of the present disclosure, a tampon applicator including a moisture-activated composition is disclosed. The composition includes a hydrophobic carrier and a high molecular weight polymer having a molecular weight of between about 850,000 and 8,000,000 daltons.

In another embodiment of the present disclosure, a tampon applicator including a moisture-activated composition is disclosed. The composition is an emulsion including mineral oil, a high molecular weight sodium polyacrylate having a molecular weight of about 5,000,000 daltons, $C_{12}$-$C_{15}$ Pareth-7, and sorbitan monooleate.

In yet another embodiment of the present disclosure, a method for reducing the coefficient of friction during use of a tampon applicator is disclosed. The method includes applying a composition to a tampon applicator and contacting the tampon applicator with a mucosal surface. The composition includes a hydrophobic carrier and a high molecular weight polymer having a molecular weight of between about 850,000 and 8,000,000 daltons. Upon contact with the mucosal surface, the composition on the tampon applicator is activated, thereby reducing the coefficient of friction between the tampon applicator and the mucosal surface.

Other features of the present disclosure will be in part apparent and in part pointed out hereinafter.

BRIEF DESCRIPTION OF THE DRAWINGS

Corresponding reference characters indicate corresponding parts throughout the drawings.

DETAILED DESCRIPTION

In one embodiment of the present disclosure, a personal care device includes a moisture-activated composition. The composition generally includes a hydrophobic carrier and a high molecular weight polymer having a molecular weight of between about 850,000 and 8,000,000 daltons. In one particularly suitable embodiment, the composition includes mineral oil, a high molecular weight sodium polyacrylate having a molecular weight of about 5,000,000 daltons, $C_{12}$-$C_{15}$ Pareth-7, and sorbitan monooleate.

A. Definitions

The term "use", as used herein with reference to the use of a personal care device, generally refers to the insertion, removal, and overall wearing of the personal care device. For example, when the personal care device is a vaginal tampon, the "use" of the tampon includes insertion of the tampon into the vagina, the period of time the tampon is worn within the vagina, and the removal of the tampon from the vagina.

The term "moisture-activated composition" as used herein generally refers to a composition that becomes active only upon contact with moisture, such as, for example, water or a user's bodily fluids.

The phrase "mucosal surface" refers to linings of a body that are involved in absorption and secretion of bodily fluids.

The phrase "vaginal secretions" refers to any moisture or fluid that is created by glands inside the vagina and/or cervix and is secreted from mucosal surfaces. Such secretions include, for example, menses.

The phrase "reduced soiled appearance" as used herein refers to the personal care device, and particularly, a vaginal tampon, having a cleaner, less messy, appearance.

B. Personal Care Device

The personal care device of the present disclosure may be any suitable personal care device known or used in the personal hygiene industry. For example, the personal care device may be a tampon, a tampon applicator, or a combination thereof. Alternatively, the personal care device can be a pad, a liner, a diaper or a medical device such as an endotracheal tube.

As used herein, "tampon" may refer to any absorbent material intended for use in absorbing bodily fluids. Exemplary tampons are vaginal tampons and nasal tampons, with vaginal tampons being particularly suitable for use with the composition described herein. The vaginal tampons can be used in combination with a tampon applicator or alone as a digital vaginal tampon.

Figure 1:
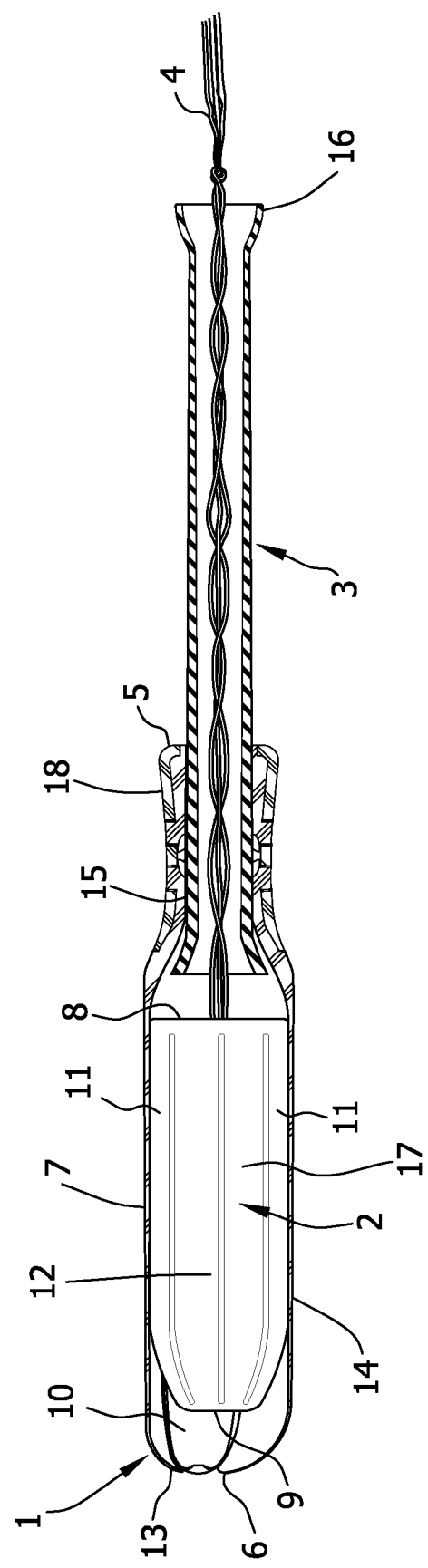
FIG. 1 is an exemplary embodiment of a personal care device of the present disclosure.

An exemplary personal care device for use with the moisture-activated composition is illustrated in FIG. 1. Specifically, in FIG. 1, a tampon 1 housed in a tampon applicator 1 is disclosed. The tampon applicator 1 is illustrated and described in connection with the tampon 2 such as described throughout this disclosure for insertion into the vagina of a user to absorb menses, blood and other bodily fluids. It is understood, however, that the tampon applicator 1 may be used in connection with other suitable types of tampons without departing from the scope of this disclosure.

The tampon applicator 1 can be any suitable tampon applicator 1 used in the personal hygiene industry. For example, the tampon applicator may include an applicator barrel 7 (which houses the tampon) and a plunger 3.

As shown in FIG. 1, in one embodiment, the tampon applicator 1 includes an applicator barrel 7. The barrel 7 is generally elongated and cylindrical, having a lower end 5 and an upper end 6. When the tampon applicator 1 includes a barrel 7, the applicator barrel 7 may be suitably constructed of one or more materials as generally known in the art. Exemplary materials for use in the applicator barrel 7 include polyolefins such as, without limitation, polypropylene, polyethylene, low density polyethylene, high density polyethylene, linear low density polyethylene, near low density polyethylene, polyethylene terephthalate (PET), nylon, polystyrene, polyvinyl chloride, polymethyl methacrylate, polyolefin elastomer, copolymers of alfa-olefins, and combinations thereof. In some particularly suitable embodiments, the applicator barrel 7 is formed of a low density polyethylene or a polymeric blend that includes low density polyethylene, such as a combination of low density polyethylene and at least one of linear low density polyethylene or a high density polyethylene.

In one embodiment, the barrel 7 is constructed of two different materials, a first material that includes the tip region 13, central region 14 and an underlying portion of the grip region 15, and a second material that includes the overlayer portion of the grip region 18.

The tampon applicator 1 in accordance with the present disclosure may also include a plunger 3. A plunger 3 can be used to push the tampon 2 out of the tampon applicator 1 and into the vagina. Specifically, the plunger 3 is movable telescopically relative to the applicator barrel 7 to expel the tampon 2 from the barrel 7.

The plunger 3 can be elongated and is suitably hollow so that when a withdrawal string 4 is attached to the tampon 2, the string 4 may extend out through an outer end 16 of the plunger 3. It should be understood, however, that the plunger 3 need not be hollow, and that the withdrawal string 4 may extend other than through the plunger 3 without departing from the scope of this disclosure. A substantial length of the plunger 3, extending to the outer end 16 thereof, is accessible exterior of the applicator barrel 7 in the extended position of the plunger 3 for gripping by the user to move the plunger 3 relative to the barrel 7. The plunger 3 can have an increased outer diameter adjacent its outer end 16, such as in the form of a flange, ring, bell-shape or other suitable shape to facilitate gripping of the plunger 3 and to act as a stop to inhibit the outer end 16 of the plunger 3 from fully entering the applicator barrel 7.

The plunger 3 can be, in one particularly suitable embodiment, constructed of the same material (e.g., polymer or polymeric blend) as the applicator barrel 7. While not shown in the drawings, it is contemplated that the plunger 3 may be formed by a co-injection process similar to that typically used to form the applicator barrel 7 so that an overlayer is applied to the plunger 3, such as at or adjacent the outer end 16 of the plunger 3 to facilitate enhanced gripping of the plunger 3 during use. It is also contemplated that the end 16 of the plunger 3 may be constructed to have a relatively smooth or polished outer surface and, as such, have a different surface roughness and/or visual appearance as compared to the rest of the plunger 3.

Housed within the tampon applicator 1, and particularly the applicator barrel 7, is the tampon 2. The tampon 2 has a pledget 17 and a withdrawal string 4 attached thereto, generally adjacent a lower end 8 of the pledget 17 for use in pulling the pledget 17 from the vagina. A gap 10 can be present between the applicator upper end 6 and the pledget upper end 9.

The structure of a tampon 2 is known in the art and includes an absorbent body, generally known as a pledget 17. The pledget 17 may include any absorbent materials known for use in the absorbent body of tampons. In one embodiment, the absorbent body of the tampon includes a mixture of cotton fibers and rayon fibers, which are formed into a soft batt by airlaying or carding and enclosed in a bonded carded web. Bonded carded webs are well known and generally include rayon fibers bonded by saturation, printing or coating with a polyvinyl acetate. Non-woven scrim construction and spun-bonded webs may also be used for the batt-enclosing wrapper. Ranges of fiber mixtures of from about 50% to about 70% by weight cotton and about 30% to about 50% by weight rayon have been found particularly suitable.

In addition to the cotton-rayon fiber mixture, super-absorbent fibers or powders may also be added to the pledget 17. A suitable range of about 3% to about 10%, by weight, super-absorbent materials have been found useful. In one particular embodiment, the fibers of the pledget 17 include about 50% by weight cotton, about 40% by weight rayon and about 10% by weight super-absorbent fibers.

In another embodiment, the absorbent body of the pledget 17 may include rayon polyacrylate fibers, as well as various sponge-like absorbent materials such as cellulose sponges, and cross-linked polyurethane or polyester foams.

The pledget 17, incorporating any of these materials, must be capable of being compressed to a self-sustaining form which is releasable when contacted by bodily fluids during use.

As noted above, the tampon 2 may further include a withdrawal string 4 fastened to the pledget 17 generally adjacent an outer or trailing end thereof for use in pulling the pledget 17 from the vagina during removal. Suitable withdrawal string 4 materials and constructions are known to those skilled in the art.

C. Moisture-Activated Composition

Referring now to the moisture-activated composition used with the personal care devices of the present disclosure, the composition generally includes a hydrophobic carrier and a high molecular weight polymer having a molecular weight of between about 850,000 and 8,000,000 daltons.

The hydrophobic carrier in the composition acts as a carrier material for the solids included in the composition. In some embodiments, the concentration amount of the hydrophobic carrier may be increased in order to dilute the solids content of the composition. The composition can include from about 0.01% to about 99.9%, by weight, of the hydrophobic carrier. Preferably, the composition includes from about 0.10% to about 90% and more preferably from about 1% to about 70%, by weight, of the hydrophobic carrier.

Suitable hydrophobic carriers for use in the present disclosure include synthetic oils (e.g., mineral oil), natural oils (e.g., sunflower oil), esters (e.g., isopropyl myristate), silicone oils (e.g., dimethicone), and the like. In a preferred embodiment of the present disclosure, the hydrophobic carrier is mineral oil.

It has now been found that the use of a high molecular weight polymer, particularly a polymer having a molecular weight of between about 850,000 and 8,000,000 daltons, in the composition of the present disclosure provides a moisture-activated composition that may be applied to a personal care device such as a tampon and/or tampon applicator. The composition becomes lubricious only after contact with moisture such as from contact with vaginal secretions, allowing for easier, more comfortable, insertion, wear and removal of the personal care device. The composition keeps its lubricious consistency even during lighter flow days when there is less moisture present on the mucosal surfaces.

Further, when the moisture-activated composition including the high molecular weight polymer is applied to a tampon, the tampon has a much cleaner, less soiled appearance. More particularly, the tampon will appear very light pink in color where, in the past, tampons had a dark red color upon removal.

It has been discovered that the composition including a high molecular weight polymer having a molecular weight within the above-described ranges becomes lubricious only after contact with moisture. Accordingly, the composition is dry to the touch prior to activation, while activating upon contact with moisture to allow for easier, more comfortable, insertion, wear and removal of the personal care device. Compositions including polymers having higher or lower molecular weights than described either become tacky and sticky upon contact with moisture or fail to become lubricous at all.

Typically, the high molecular weight polymer used in the composition of the present disclosure has a molecular weight of between about 850,000 to about 8,000,000 daltons. More suitably, the high molecular weight polymer has a molecular weight of from about 1,300,000 to about 7,000,000 Daltons, and even more suitably, from about 3,000,000 to 6,000,000 Daltons. In one specific embodiment, the high molecular weight polymer has a molecular weight of about 850,000 daltons. In another specific embodiment, the high molecular weight polymer has a molecular weight of about 1,300,000 daltons. In one particularly preferred embodiment, the high molecular weight polymer has a molecular weight of about 5,000,000 Daltons.

The high molecular weight polymer in the composition is a high molecular weight polymer that acts as a polymeric surface enhancer, film former, surface modifier and/or a moisture-activated lubricity enhancer. In a preferred embodiment of the disclosure, the high molecular weight polymer is high molecular weight sodium polyacrylate having a molecular weight of about 5,000,000 daltons. Other suitable high molecular weight polymers are sodium polyacrylate with molecular weight from about 7,000,000 to about 8,000,000 daltons, as well as polyvinylpyrrolidone having a molecular weight of from 850,000 to 1,300,000 Daltons.

In one embodiment of the present disclosure, the composition includes from about 1% to about 60%, by weight, of the high molecular weight polymer, including from about 6% to about 25%, by weight, of the high molecular weight polymer. In specific embodiments of the present disclosure, the composition includes about 1.5%, about 6.5%, about 12.5%, or about 25%, by weight, of the high molecular weight polymer. In a particularly preferred embodiment of the present disclosure, the composition includes about 1.5%, by weight, of the high molecular weight polymer.

In another embodiment of the present disclosure, the composition further includes one or more surfactants. The surfactant used in the composition lowers the surface tension of the composition, which allows easier spreading of the composition. The surfactant may also lower the interfacial tension between the hydrophobic carrier and other solids in the composition. The composition may include from about 0.01% to about 40%, including from about 0.05% to about 35%, and including from about 0.1% to about 30%, by weight, of the surfactant. Preferably, the composition includes from about 0.1% to about 25%, more preferably from about 0.1% to about 15%, and even more preferably from about 0.1% to about 10%, by weight of the surfactant.

Suitable surfactants may include anionic surfactants, zwitterionic surfactants, amphoteric surfactants and nonionic surfactants. Examples of suitable anionic surfactants include, but are not limited to tea-stearate, sodium laurate, sodium lauryl sulfate, sodium laureth sulfate, disodium sulfosuccinate, sodium methyl cocoyl taurate, ammonium acyl sarcosinate, sodium cocoyl isethionate, sodium stearoly lactylate, sodium trideceth-13 carboxylate, dilaureth-4 phosphate, and the like. Examples of amphoteric and zwitterionic surfactants, include, but are not limited to cocamidopropyl betaine, sodium cocoamphoacetate, aminopropyl alkyglutamide, and the like.

Examples of suitable nonionic surfactants include poloxamer 231, poloxamer 182, poloxamer 184, Brij® 30 (polyoxyethylene (4) lauryl ether), Brij® 93 (polyoxyethylene (2) oleyl ether), Brij® 96 (polyoxyethylene (20) oleyl ether), Brij® 99 (polyoxyl (10) oleyl ether), Span® 20 (sorbitan monolaurate), Span® 40 (sorbitane monopalmitate), Span® 60 (sorbitane monostearate), Span® 80 (sorbitane monooleate), Span® 85 (sorbitane trioleate), TWEEN® 20 (polyethylene glycol sorbitan monolaurate; polyoxyethylene (20) sorbitan monolaurate), TWEEN® 40 (polyoxyethylene (20) sorbitan monopalmitate), TWEEN® 60 (polyethylene glycol sorbitan monostearate; polyoxyethylene (20) sorbitan monostearate), TWEEN® 80 (polyethylene glycol sorbitan monooleate; polyoxyethylene (20) sorbitan monooleate), Myrj® 45 (polyoxyethylene (8) stearate), Myrj® 51 (polyoxyethylene stearate), Myrj® 52 (polyoxyethylene stearate), and Miglyol 840 (propylene glycol dicaprylate/dicaprat), among others.

Surfactants according to the present disclosure are not particularly limited and will preferably have a hydrophilic/lipophilic balance (HLB) of from 0 to 20. In one embodiment, a low HLB surfactant (HLB of from 0-10) can be used in combination with a high HLB surfactant (HLB of from 10-20) to stabilize the composition. For example, in one particularly suitable embodiment, the surfactants that may be used in accordance with the present disclosure are sorbitan monooleate (HLB 4.3) and $C_{12}$-$C_{15}$ Pareth-7 (HLB 12.3).

In yet another embodiment of the present disclosure, the composition includes from about 0.01% to about 50%, by weight, water, without instability, swelling of the high molecular weight polymer, or swelling of the absorbent personal care device.

In one particularly preferred embodiment, the composition is an emulsion, such as a water-in-oil emulsion, containing the hydrophobic carrier, high molecular weight polymer, one or more surfactants, and water.

Typically, the composition has a pH of from about 2 to about 12, preferably from about 3 to about 10, and more preferably from about 4 to about 10.

D. Application of Composition to Personal Care Device

With reference again to FIG. 1, the personal care device of the present disclosure may be a tampon 2, a tampon applicator 1, or a combination of the tampon 2 and the tampon applicator 1. The moisture-activated composition of the present disclosure can be applied on any surface of the personal care device.

1. Application to the Tampon

When the personal care device is a tampon 2, the tampon 2 can include the composition on any suitable component of the tampon 2, such as the pledget 17 and the withdrawal string 4. More particularly, the entire pledget 17 (including the upper and lower ends 8, 9, and pledget sides 11) may include the moisture-activated composition or, alternatively, only one of the ends 8, 9 or sides 11 may include the composition. In one embodiment, the outer surface 12 of the pledget 17 may include the moisture-activated composition. In another embodiment, both the inner surface (not shown) and the outer surface 12 of the pledget 17 may include the composition.

In one embodiment, the moisture-activated composition may be applied to the tip of the tampon 2 and extends to a mid-length point on the tampon 2. In another embodiment, the composition may be applied to the full-length of the tampon 2.

2. Application to the Tampon Applicator

When the personal care device of the present disclosure is a tampon applicator 1, the tampon applicator 1 may include the composition on any suitable component of the tampon applicator 1, such as, for example, an applicator barrel 7 and a plunger 3. The composition may be included on any one component, in whole or in part, of the tampon applicator 1 without departing from the scope of the disclosure.

In some embodiments, application of the moisture-activated composition to the tampon applicator may be achieved in two different steps. Specifically, the surface of the applicator may be pretreated with a chemical composition prior to application of the moisture-activated composition. Alternatively, the surface of the applicator may be altered by scorching/scoring of the surface by mechanical (e.g., sandpaper) or chemical processes prior to application of the moisture-activated composition. These pretreatment steps may allow the moisture-activated composition to better adhere to the surface of the applicator.

3. Method of Application

To apply the composition to the personal care device, the composition may generally be applied using any means known in the art so long as the application method does not render the composition useless for its intended purpose. Exemplary methods for applying the composition include brush coating, hand dipping, rolling, spraying, and combinations thereof. The composition is typically allowed to dry prior to use. Upon drying, the composition is non-tacky and/or non-sticky to the touch.

In one embodiment of the present disclosure, the moisture-activated composition may be applied to a personal care device in any pattern known in the art to create a design on the device. Exemplary patterns of the present disclosure include rows, swirls, dots and/or lines on the surface of the personal care device. Such an application pattern will decrease the insertion and removal frictional forces and the differing patterns may further provide differing amounts of friction reduction depending on the orientation of the patterns on the personal care device.

In one embodiment of the present disclosure, the moisture-activated composition can be applied (i.e., via patterns (e.g., dots, etc.) through brush coating, hand dipping, rolling or spraying) either before assembly of the complete tampon or after assembly of the complete tampon. The moisture-activated composition can be applied either directly to the tampon absorbent material or, if a coverstock is used, to a coverstock that covers the absorbent material of the tampon prior to the assembly of the finished tampon.

In one embodiment of the present disclosure, the moisture-activated composition is applied to the personal care device at an amount of from about 0.01% to 200%, including from about 0.05% to about 150%, and including from about 0.1% to about 100%, by weight, of the personal care device. Preferably, the moisture-activated composition is applied to the personal care device at an amount of from about 1% to about 95%, more preferably from about 5% to about 90%, and even more preferably about 50%, by weight, of the personal care device.

E. Methods of Use

The present disclosure is additionally directed to a method of reducing the coefficient of friction during use of a personal care device. In the personal hygiene industry, one barrier to the use of personal care devices is the discomfort experienced during insertion, wear, and removal of the personal care device.

The present disclosure alleviates this discomfort by providing a moisture-activated composition that is applied to a personal care device and becomes lubricious only after contact with moisture such as from contact with bodily fluids (e.g., vaginal secretions) present on mucosal surfaces of the user. This provides a user with easier, more comfortable, insertion, wear and removal of the personal care device.

In one embodiment, for example, the moisture-activated composition is applied to a personal care device such as a vaginal tampon. As the tampon is inserted within the vagina, the tampon, including the composition, contacts moisture in the form of vaginal secretions from the mucosal surfaces, thereby activating the composition. Upon activation, the composition becomes lubricious, thereby reducing the coefficient of friction between the vaginal mucosal surfaces and the surface of the tampon. This decreased friction makes the insertion of the personal care device more comfortable and more desirable to the user.

Likewise, while the tampon is being removed from the vagina, moisture from vaginal secretions, which are in contact with the composition on the tampon, will reduce the coefficient of friction between the vaginal mucosal surfaces and the tampon's surface. This decreased friction makes the removal of the personal care device more comfortable and more desirable to the user.

One benefit of the composition used in the present disclosure is that the composition keeps its lubricious consistency even during lighter flow days when there is less moisture present on the mucosal surfaces, allowing for a more comfortable removal of the tampon even during these periods. In one embodiment of the present disclosure, the amount of moisture needed to activate the composition is from about 0.1 mg to about 10 g. Preferably, the amount of moisture needed to activate the composition is from about 1 mg to about 5 g. This amount of moisture is the amount typically present during menstruation and includes, for example, vaginal secretions.

While described herein with respect to the tampon, it should be recognized that the composition may be applied to one of the tampon applicator barrel and/or the plunger of the tampon applicator, to allow for a reduced coefficient of friction between the vaginal mucosal surfaces and the applicator barrel and/or plunger similar to the tampon described above. Similar to the tampon, this reduced coefficient of friction will improve insertion and removal of the tampon applicator.

Additionally, in one specific embodiment, when the personal care device is a tampon applicator, the moisture-activated composition may be applied to the applicator to provide a cue to the user of how far to insert the applicator. Specifically, when the user inserts the applicator, and the composition becomes lubricious after activation, the user will feel the slippery surface where the moisture-activated composition is located on the applicator. Once the user reaches the point on the applicator where the lubricious composition stops and a dry, more frictional surface of the applicator is sensed, the user has a cue to deploy the plunger and to not insert the applicator further into the vagina. This, in turn, allows for the user to avoid any unnecessary frictional forces between the personal care device and the vagina.

In one embodiment of the present disclosure, in addition to reducing the coefficient of friction during use, the composition can be used to reduce the soiled appearance of a tampon after removal. Generally, after a tampon is used, the tampon becomes bloody and soiled in appearance. When the moisture-activated composition of the present disclosure is applied to a tampon, however, the tampon is much cleaner and has a much less soiled appearance. For example, the tampon will appear a very light pink color where, in the past, tampons had a dark red color upon removal. As treatment with the moisture-activated composition results in the tampon being cleaner and less soiled in appearance, consumer perception of the tampon may further be improved.

One further unexpected advantage of the moisture-activated composition used in the personal care devices of the present disclosure is that the composition may be applied without significantly reducing the absorbency of the tampon.

Absorbency Test Method

Tampons come in several sizes, each size corresponding to a range of fluid they can absorb. If the tampon absorbs less than this range of fluid, it will not pass the FDA test for tampon absorbency (21 C.F.R. 801.430—User Labeling for Menstrual Tampons). The FDA Test verifies how much a size-specific tampon can absorb. In one embodiment of the present disclosure, when the moisture-activated compositions of the present disclosure are applied to a tampon, the absorbency of the tampon may be decreased by less than 15% according to the FDA test. Alternatively, in another embodiment, the absorbency of the tampon may be decreased by less than 5% according to the FDA test.

This is a significant result of the present disclosure, as conventional polymer blends cause the tampon to swell, which can lead to discomfort during use of the tampon.

The present disclosure is illustrated by the following Examples, which are merely for the purpose of illustration and are not to be regarded as limiting the scope of the disclosure or manner in which it may be practiced.

EXAMPLES

Coefficient of Friction Testing Method

In accordance with the Examples of the present disclosure, the coefficient of friction ("COF") of personal care devices including the moisture-activated composition was tested. The testing provided how lubricous and/or slippery the personal care devices became once the compositions applied thereto become activated (i.e., lubricious) with moisture.

In order to conduct the coefficient of friction testing, a synthetic vaginal model was used in combination with an Instron device. The vaginal model was placed within the Instron device, specifically a Sintech 500/S device manufactured by MTS in Eden Prairie, Minn., and the Sintech 500/S device measured the compression and decompression forces of the personal care device within the vaginal model. The Instron device included a housing unit that accommodated the vaginal model while mounted to the Instron device. The housing unit held the vaginal model in such a manner so that the vaginal model was accessible for insertion and removal of tampons by the Instron device probe. Set screws were used to hold the vaginal model encased in the housing unit, as well as to adjust the pressure the housing unit applied to the vaginal model. By adjusting the pressure applied to the vaginal model, the various in vivo pressures that occur within a user's vagina could be replicated.

The surface of the vaginal model was covered with collagen film, which was equilibrated in a TAPPI (Technical Association of the Pulp and Paper Industry) room which was similar to the environment of the vaginal mucosal surface. The TAPPI room conditions were 23° C.+1°/50% RH+/−2%.

For the following Examples, the moisture-activated composition was applied to a digital tampon at various concentration ranges. The tampons were then contacted with water via a hand pump spray. Each spray from the hand pump produced from about 0.1 g to about 0.15 g of water, wherein about 0.001 g to about 0.1 g of water contacted the surface of the tampon. After just two sprays from the hand pump spray, the tampons were inserted and removed from the vaginal model, and the resulting coefficient of friction measurements were obtained.

Figure 2:
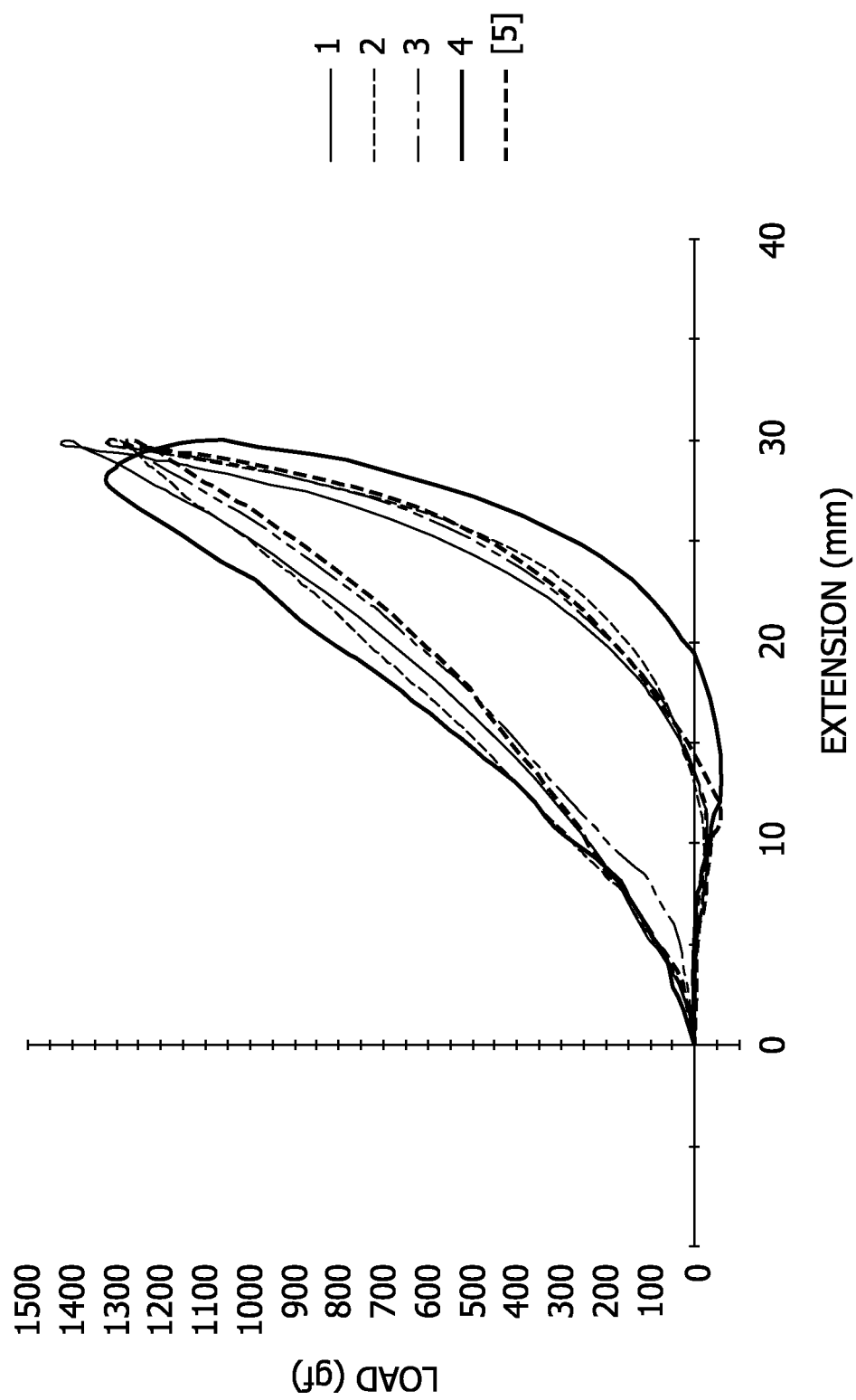
FIG. 2 is a graphical depiction of the coefficient of friction as measured upon insertion and removal of a personal care device without the moisture-activated composition of the present disclosure coated thereon.

FIG. 2 depicts the compressional and decompressional forces experienced by five control tampons. The control tampons were untreated digital tampons inserted into the vaginal model to establish a baseline measurement. The graph in FIG. 2 depicts the grams of compression required to insert the control tampon into the model as well as the force to decompress/remove the tampon from the model.

Example 1

Figure 3:
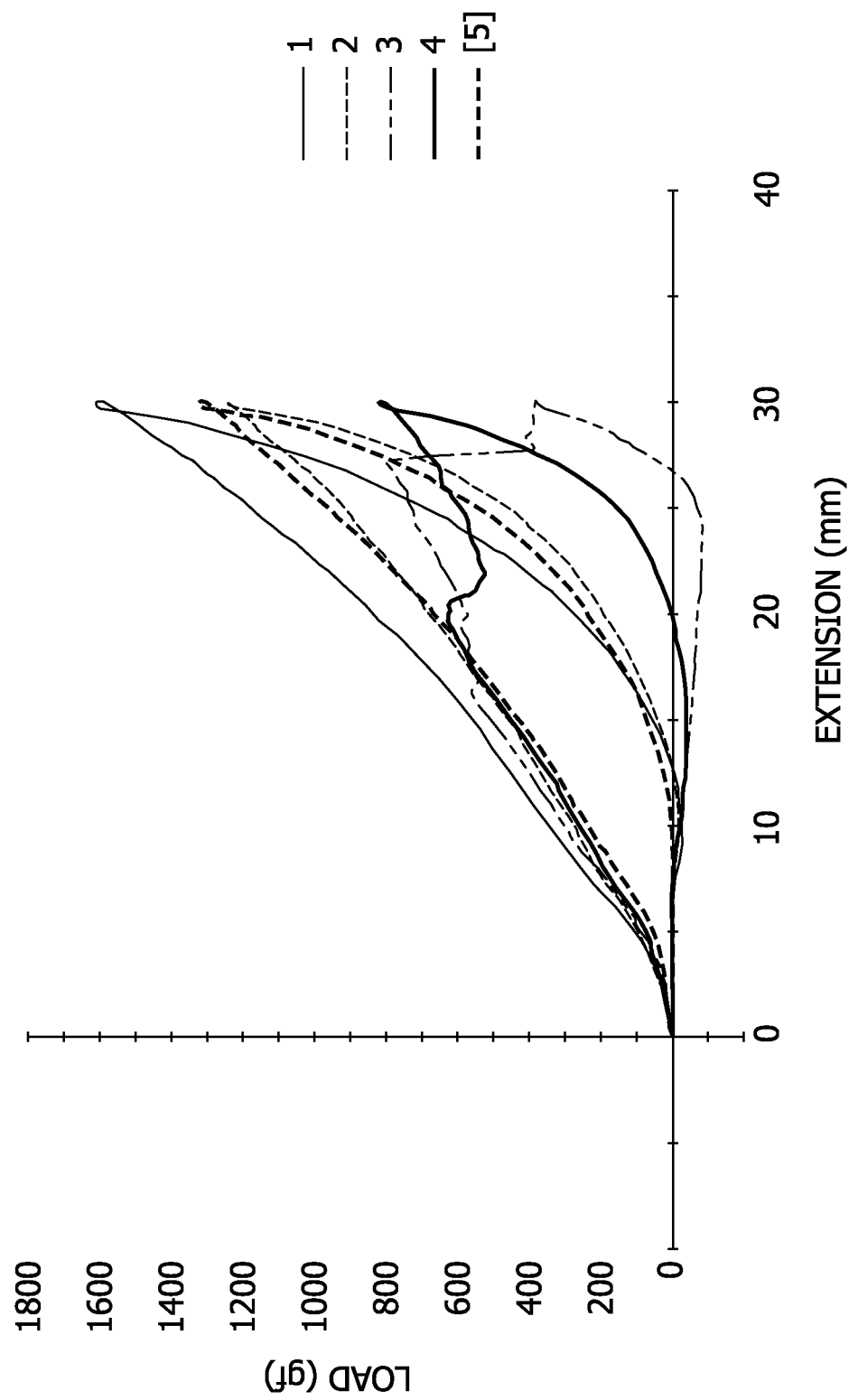
FIG. 3 is a graphical depiction of the coefficient of friction as measured upon insertion and removal of a personal care device as evaluated in Example 1.

FIG. 3 depicts an exemplary embodiment of the present disclosure, wherein the moisture-activated composition present on the tampons included, after dilution with mineral oil, a high molecular weight sodium polyacrylate (molecular weight of about 5,000,000 daltons) at an amount of about 1.25%, by weight, of the composition. As shown in FIG. 3, the amount of compression and decompression required to insert and remove the tampon from the vaginal model is decreased on the two treated tampons (Sample 4 and Sample 5) compared to the three control, untreated tampons (Samples 1, 2 and 3).

Example 2

Figure 4:
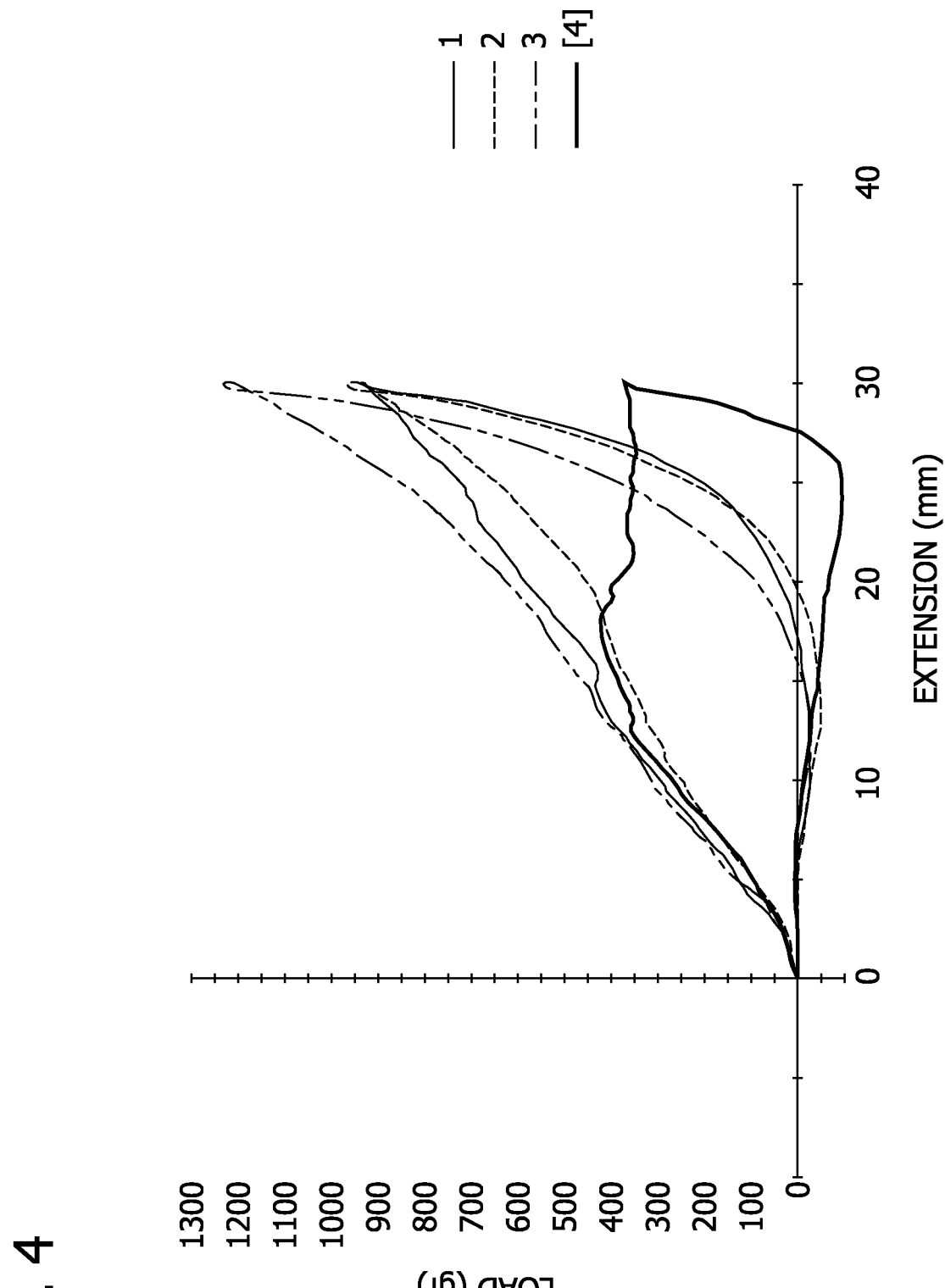
FIG. 4 is a graphical depiction of the coefficient of friction as measured upon insertion and removal of a personal care device as evaluated in Example 2.

FIG. 4 depicts an exemplary embodiment of the present disclosure, wherein the moisture-activated composition present on the tampons included, after dilution with mineral oil, a high molecular weight sodium polyacrylate (molecular weight of about 5,000,000 daltons) at an amount of about 6.5%, by weight, of the composition. As shown in FIG. 4, the amount of compression and decompression required to insert and remove the treated tampon (Sample 4) from the vaginal model is decreased compared to the control, untreated tampons (Samples 1, 2, and 3).

Example 3

Figure 5:
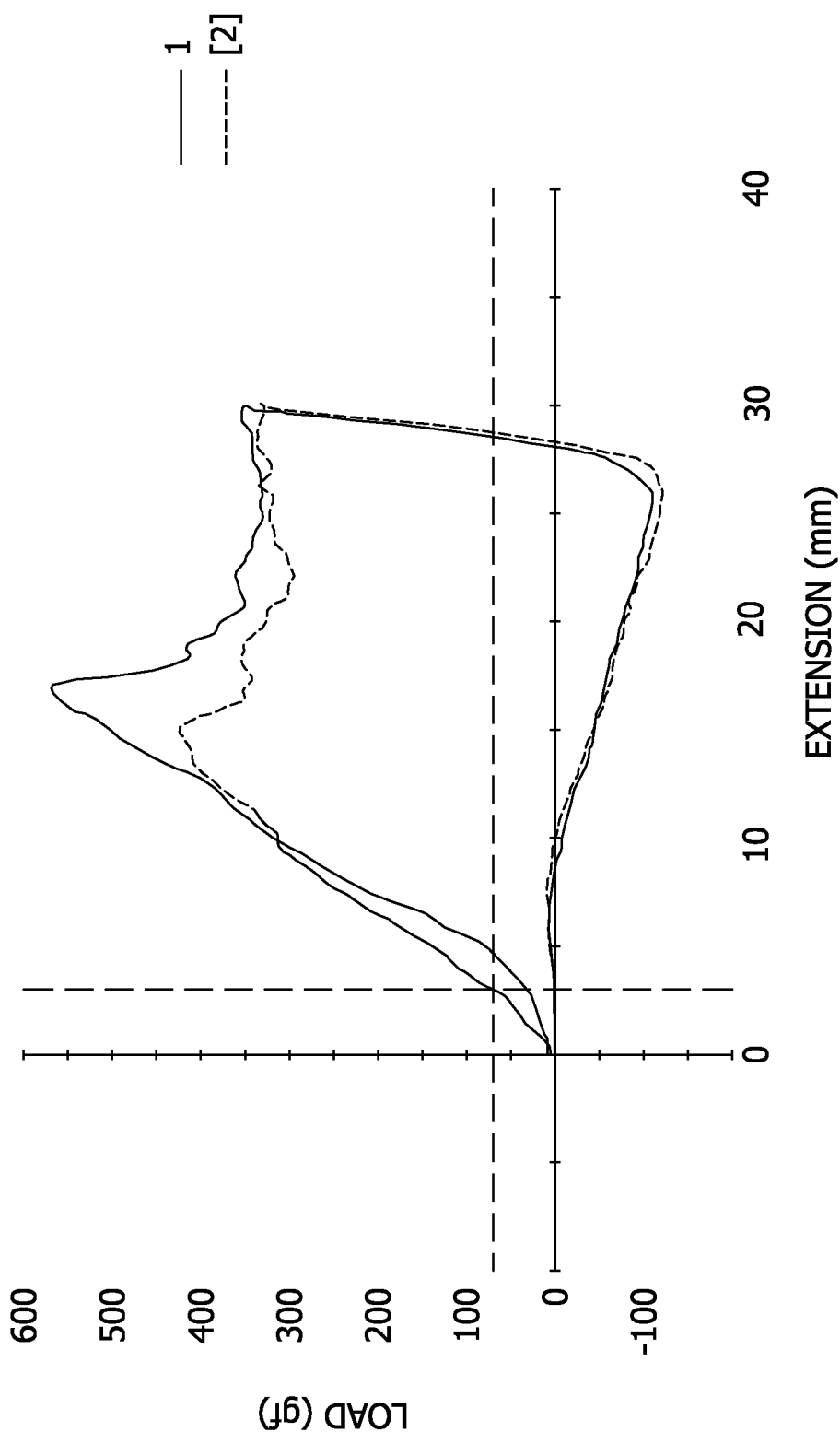
FIG. 5 is a graphical depiction of the coefficient of friction as measured upon insertion and removal of a personal care device as evaluated in Example 3.

FIG. 5 depicts an exemplary embodiment of the present disclosure, wherein the moisture-activated composition present on the tampons included, after dilution with mineral oil, a high molecular weight sodium polyacrylate (molecular weight of 5,000,000 daltons) at an amount of about 12.5%, by weight, of the composition. As shown in FIG. 5, the amount of compression and decompression required to insert and remove the treated tampon (Sample 2) from the vaginal model is decreased compared to the control, untreated tampon (Sample 1).

Example 4

Figure 6:
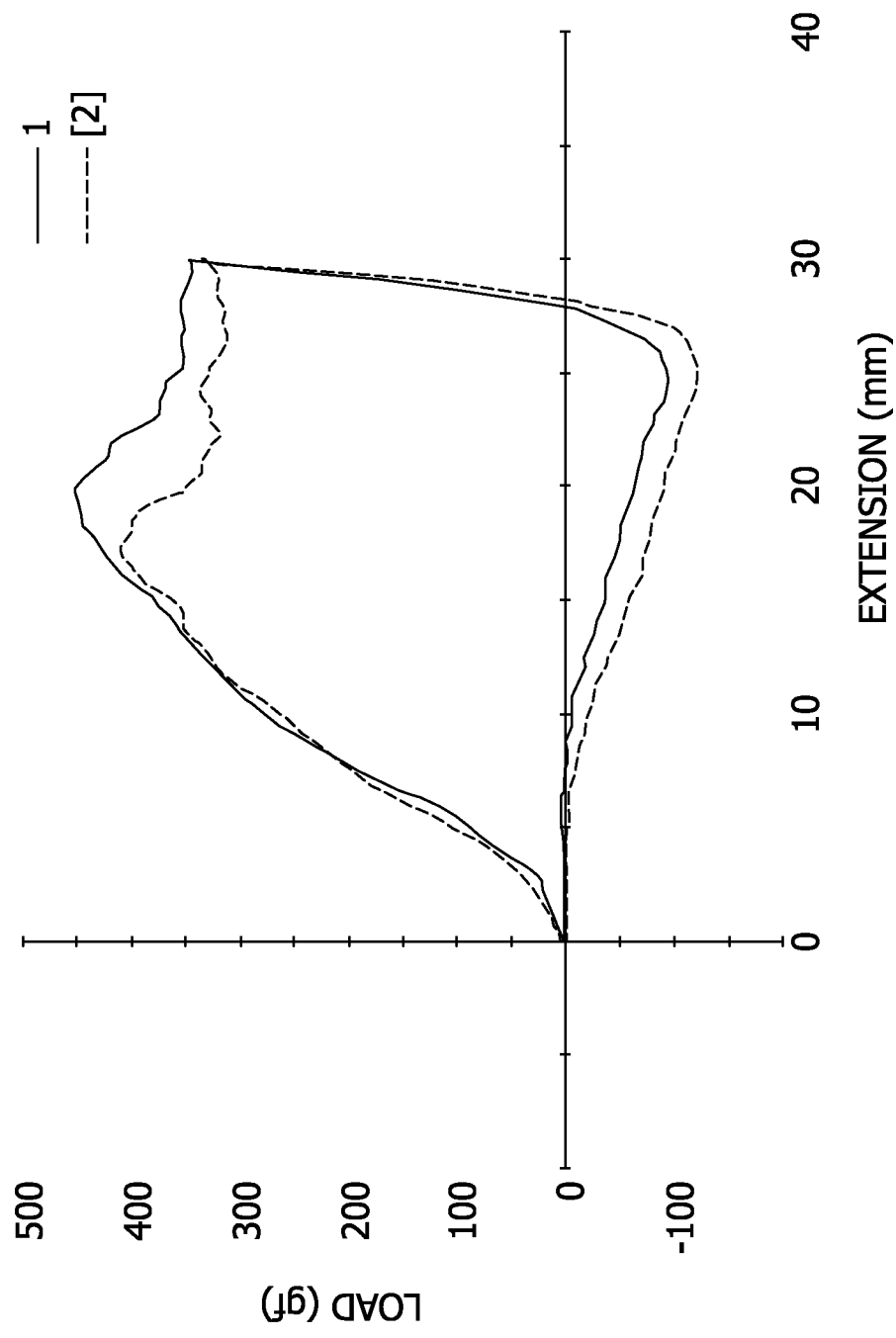
FIG. 6 is a graphical depiction of the coefficient of friction as measured upon insertion and removal of a personal care device as evaluated in Example 4.

FIG. 6 depicts an exemplary embodiment of the present disclosure, wherein the moisture-activated composition present on the tampons included a high molecular weight sodium polyacrylate (molecular weight) at an amount of about 25%, by weight, of the composition. In this Example, the composition is applied "neat," and is not diluted with any mineral oil. As shown in FIG. 6, the amount of compression and decompression required to insert and remove the treated tampon (Sample 2) from the vaginal model is decreased compared to the control, untreated tampon (Sample 1).

Results

As shown in FIGS. 2-6, when the composition was applied to the tampons, and the composition had been activated by moisture (in these examples, only approximately 0.2-0.3 g of water were sprayed, of which approximately 0.001-0.1 g of water remained on the tampon), the composition became lubricious and the tampons required less compression and decompression when inserted and removed from the vaginal model. Thus, the moisture-activated composition reduced the coefficient of friction during the use of the tampons.

In each Example shown, the moisture-activated composition reduced the coefficient of friction of the tampon. The biggest improvement was seen when the moisture-activated composition was applied to the tampons with a high molecular weight sodium polyacrylate (molecular weight of about 5,000,000 daltons) present in the composition at about 12.5% and about 25%, by weight, of the composition. In particular, FIGS. 5 and 6 show about a ⅔ reduction in compressional and decompressional forces required to insert and remove the tampons when compared to the untreated control tampons (as illustrated in FIG. 2).

Example 5

The compositions of the present disclosure may also be used to reduce the soiled appearance of a tampon after removal. In accordance with a FDA testing method known in the art (21 C.F.R. 801.430—User Labeling for Menstrual Tampons) for determining the absorbency rate of tampons, control tampons and tampons treated with the compositions of the present disclosure were examined. It was observed that the treated tampons had a less soiled appearance than the control tampons. To measure this difference, colorimetry was employed. The colorimeter equipment used for the measurements was a Byk-Gardener Color-Guide Sphere 45/0 Cat No. 6830 with color settings from CIELab and Illum/obs 65/10°. The treated tampons were dipped into a moisture-activated composition comprising a hydrophobic carrier (mineral oil) and a high molecular weight sodium polyacrylate having a molecular weight of about 5,000,000 daltons, a blend of a high HLB surfactant (C12-15 Pareth-7) and a low HLB surfactant (sorbitan monoleate), and water, and allowed to dry via hanging. The final add-on was measured after a 24-hour drying time and was found to be approximately 70% w/w of the absorbent article.

Measurements were taken using an "L," "A," "B" method where an "L" reading represented the light to dark measurement of the soiled appearance of the tampon and an "A" reading represented a red to green measurement of the soiled appearance of the tampon. The "L" readings of the control tampon averaged about a 38 while the treated tampons had "L" readings that averaged about 75. "A" readings for the control tampons averaged about 31 and "A" readings for treated tampons averaged about 15. The results are shown in the table below.

| Colorimeter Data | | | |
| --- | --- | --- | --- |
| Tampon Sample | L | A | B |
| Control Tampon | 38.4 | 30.9 | −16.92 |
| Treated Tampon | 75.75 | 14.5 | −4.28 |

These results display that that treated tampons are about twice as light in color ("L" reading) in appearance to the control tampons. Additionally, these results display that the treated tampons have a two-fold reduction in redness ("A" reading). That is, the treated tampons show about a twofold reduction in a soiled appearance over the control tampons.

Further, the results also show that the treated tampons displayed a much less intense color.

When introducing elements of the present disclosure or preferred embodiments thereof, the articles "a", "an", "the", and "said" are intended to mean that there are one or more of the elements. The terms "including", "including", and "having" are intended to be inclusive and mean that there may be additional elements other than the listed elements.

As various changes could be made in the above constructions and methods without departing from the scope of the disclosure, it is intended that all matter contained in the above description and shown in the accompanying drawings shall be interpreted as illustrative and not in a limiting sense.

What is claimed is:

1. A tampon applicator comprising a moisture-activated composition, wherein the composition comprises a hydrophobic carrier, a high molecular weight polymer having a molecular weight of between about 850,000 and 8,000,000 daltons; and $C_{12}$-$C_{15}$ Pareth-7.

2. The tampon applicator of claim 1, wherein the high molecular weight polymer has a molecular weight of about 5,000,000 daltons.

3. The tampon applicator of claim 1, wherein the composition comprises from about 1% to about 60%, by weight, of the high molecular weight polymer.

4. The tampon applicator of claim 1, wherein the high molecular weight polymer is sodium polyacrylate.

5. The tampon applicator of claim 1, wherein the composition comprises from about 0.1% to about 99%, by weight, of the hydrophobic carrier.

6. The tampon applicator of claim 1, wherein the hydrophobic carrier is mineral oil.

7. The tampon applicator of claim 1, wherein the tampon applicator comprises at least one of an applicator barrel and a plunger.

8. The tampon applicator of claim 7, wherein at least one of the applicator barrel and the plunger comprises the composition.

9. The tampon applicator of claim 1, wherein the composition further comprises a low HLB surfactant.

10. A tampon applicator comprising a moisture-activated composition, wherein the composition comprises a hydrophobic carrier; a high molecular weight polymer having a molecular weight of between about 850,000 and 8,000,000 daltons; and sorbitan monooleate.

11. The tampon applicator of claim 10, wherein the composition further comprises a high HLB surfactant.

12. The tampon applicator of claim 10, wherein the composition comprises from about 1% to about 60%, by weight, of the high molecular weight polymer.

13. The tampon applicator of claim 10, wherein the high molecular weight polymer is sodium polyacrylate.

14. The tampon applicator of claim 10, wherein the composition comprises from about 0.1% to about 99%, by weight, of the hydrophobic carrier.

15. The tampon applicator of claim 10, wherein the hydrophobic carrier is mineral oil.

16. A tampon applicator comprising a moisture-activated composition, wherein the composition is an emulsion comprising mineral oil, a high molecular weight sodium polyacrylate having a molecular weight of about 5,000,000 Daltons, $C_{12}$-$C_{15}$ Pareth-7, and sorbitan monooleate.

17. A method of reducing the coefficient of friction during use of a tampon applicator, the method comprising: applying a moisture-activated composition to the tampon applicator, the composition comprising a hydrophobic carrier; a high molecular weight polymer having a molecular weight of between about 850,000 and 8,000,000 daltons; and at least one surfactant selected from the group consisting of $C_{12}$-$C_{15}$ Pareth-7 and sorbitan monooleate; and, contacting the tampon applicator with a mucosal surface to activate the composition on the tampon applicator, wherein upon contact, the coefficient of friction between the tampon applicator and the mucosal surface is reduced.

18. The method of claim 17, wherein the high molecular weight polymer has a molecular weight of about 5,000,000 daltons.

19. The method of claim 17, wherein the high molecular weight polymer is sodium polyacrylate.

20. The method of claim 17, wherein the composition comprises from about 1% to about 60%, by weight, of the high molecular weight polymer.

* * * * *